US00PP17685P2

(12) United States Plant Patent
Austin

(10) Patent No.: US PP17,685 P2
(45) Date of Patent: May 1, 2007

(54) SHRUB ROSE PLANT NAMED 'AUSJIVE'

(50) Latin Name: *Rosa hybrida*
Varietal Denomination: AUSjive

(75) Inventor: David C. H. Austin, Wolverhampton (GB)

(73) Assignee: David Austin Roses Limited, Albrighton, Wolverhampton (GB)

( * ) Notice: Subject to any disclaimer, the term of this patent is extended or adjusted under 35 U.S.C. 154(b) by 0 days.

(21) Appl. No.: 11/263,894

(22) Filed: Oct. 31, 2005

(51) Int. Cl.
*A01H 5/00* (2006.01)

(52) U.S. Cl. ..... Plt./107
(58) Field of Classification Search ..... Plt./107
See application file for complete search history.

*Primary Examiner*—Kent Bell
*Assistant Examiner*—June Hwu
(74) *Attorney, Agent, or Firm*—Klarquist Sparkman LLP

(57) ABSTRACT

Shrub rose plant substantially as shown and described, characterized particularly by its flowers in deep, rounded, many-petalled cups of deep pink color; having an Old Rose fragrance on a rounded shrub with arching stems, medium to tall in size; and its resistance to powdery and downy mildew.

1 Drawing Sheet

Figure 1:
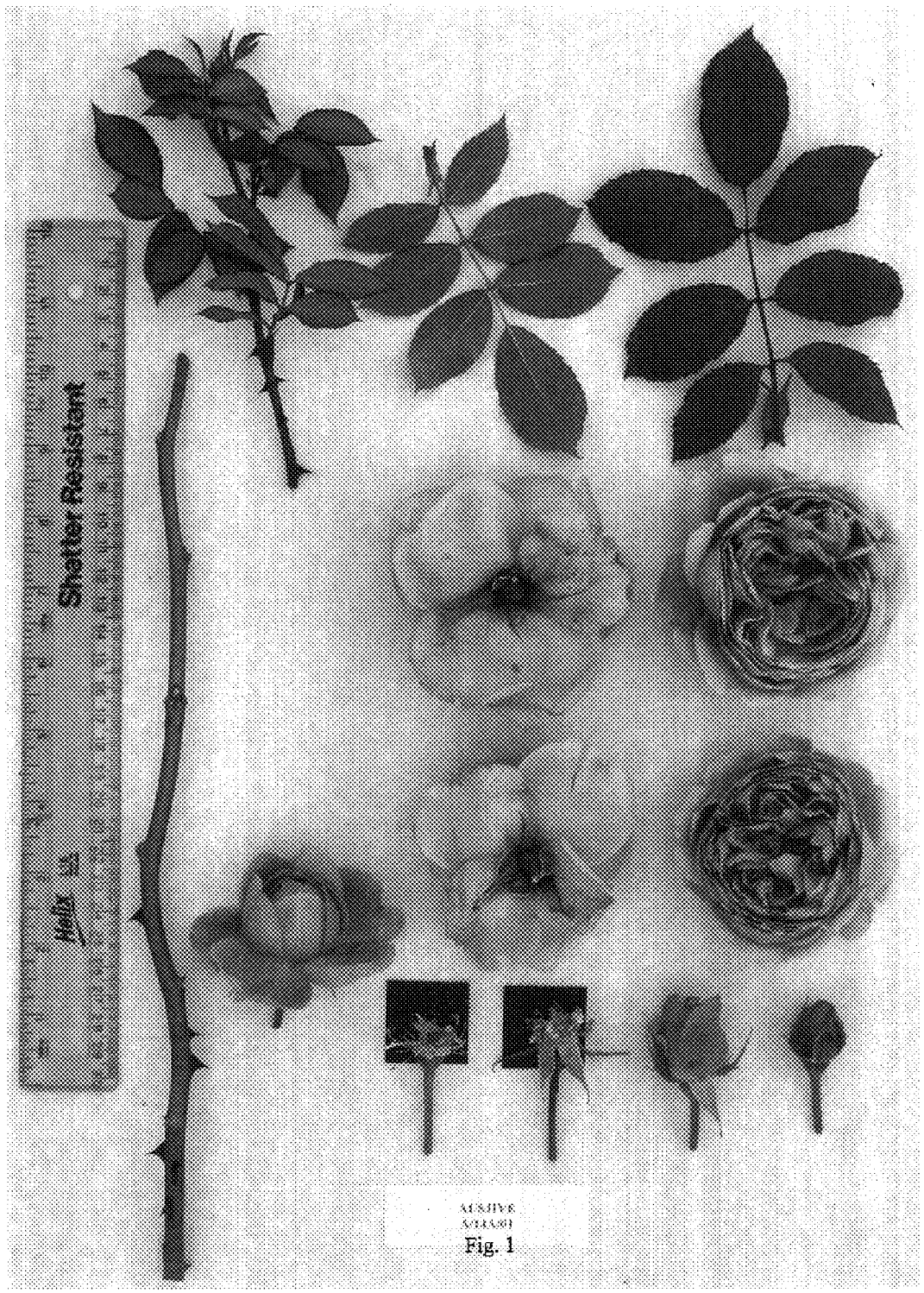

Genus and species: *Rosa hybrida.*
Variety denomination: 'AUSjive'.

ORIGIN OF THE INVENTION

The present invention relates to a new and distinct variety of a shrub rose plant named 'AUSjive' which was originated by me by crossing an unnamed, unpatented seedling with an unnamed, unpatented seedling.

BACKGROUND OF THE INVENTION

The primary objective of this breeding was to produce a very tough and healthy, repeat flowering variety with full, deep pink blooms on a rounded shrub.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Flowers in deep, rounded, many-petalled cups of deep pink color.
2. Rounded shrub with arching stems, medium to tall in size.
3. Old Rose fragrance.

Asexual reproduction of this new variety by budding, as performed at Albrighton, England, shows that the foregoing and all other characteristics and distinctions come true to form and are established and transmitted through succeeding propagations.

Comparison with Parents

The seed parent is a larger shrub than 'AUSjive' and has paler pink blooms. The pollen parent has scarlet, semi-double blooms compared with the full, deeply cupped, deep pink blooms of 'AUSjive'.

Comparison with Similar Variety

'AUStijus' has blooms that are more lilac in color with smaller, narrower petals than 'AUSjive' and a fruity fragrance. 'AUSjive' has more deeply cupped, fuller blooms with an Old Rose fragrance and has redder prickles than 'AUStijus'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling. (Unpatented).

FLOWER

Observations made from plants commencing at one year of age grown in a garden environment at Albrighton, England.

Blooming habit: Recurrent. The number of blooms per plant during the growing season is profuse, but there are too many to count.

Bud:
*Size.*—About 2.5 cm long and 1.8 cm in diameter when the petals start to unfurl.
*Form.*—The bud form is globose, pointed.
*Color.*—When sepals first divide, bud color is Red Group 48B. When half blown, the upper sides of the petals are Red-Purple Group N66C and the lower sides of the petals are with Red Group 45A.

*Sepals.*—Color: Upper surface: Green Group 143A, with Yellow-Green Group 144C at base. Lower surface: Green Group 138B. Length: 2.2 cm. Width: 0.8 cm. Shape: Subulate. Surface texture: Upper surface: Rough, glandular. Lower surface: Pubescent. There are three normally appendaged sepals. There are two unappendaged sepals with canescent edges.

*Receptacle.*—Color: Green Group 143A with irregular patches of Greyed-Purple Group 187A. Shape: Campanulate. Size: About 0.9 cm long×1 cm wide. Surface: Smooth.

*Peduncle.*—Length: Medium, averaging about 7 cm. Surface: Smooth. Color: Yellow-Green Group 148A with irregular patches of Greyed-Purple Group 187A. Strength: Weak.

Bloom:

*Size.*—Large. Average open diameter is about 8.2 cm.

*Borne.*—Several together in rounded shaped clusters of six to nine blooms.

*Form.*—When first open: Cupped. Permanence: Retains its form to the end (very outer petals curl back).

*Petalage.*—Number of petals under normal conditions: 90–100.

*Color.*—The upper sides of the petals are Red-Purple Group N66D. The reverse sides of the petals are Purple Group 75C. The base of each petal is Yellow Group 4C. The major color on the upper side is Red-Purple Group N66D.

*Variegations.*—None.

*Discoloration.*—The general tonality at the end of the first day: Overall bloom color Red-Purple Group N66D. At the end of the third day: Overall bloom color Purple Group 75C.

*Fragrance.*—Moderate, Old Rose.

Petals:

*Texture.*—Smooth.

*Size.*—Width: 3.4 cm. Length: 4.6 cm.

*Surface.*—Smooth.

*Shape.*—Obovate. Margin: Irregular, moderate undulation. Apex Shape: Obtuse. Base Shape: Cuneate. Form: Incurved, tips slightly recurved.

*Arrangement.*—Imbricated (regularly arranged, shingle-like).

*Petaloids.*—Number: 10. Color: Red-Purple Group 72D.

*Persistence.*—Petals drop off cleanly before drying.

*Lastingness.*—On the plant: Short (about 3 days). As a cut flower: Fair (about 5 days).

Reproductive parts:

*Stamens.*—Number: 118. Length: 16 mm. Anthers: Length: 4 mm. Color: Yellow-Orange Group 17C. Arrangement: Regular around styles, mixed with petaloids. Filaments: Color: Yellow Group 9C. Length: 12 mm. Pollen: Color: Yellow-Orange Group 17C.

*Pistils.*—Number: 50. Length: 10 mm. Styles: Color: Greyed-Yellow Group 160A. Length: 9 mm. Stigmas: Color: Greyed-Yellow Group 162C. Length: 1 mm.

*Hips.*—None observed.

PLANT

Form: Shrub.

Growth: Medium vigor, bushy.

Age at maturity: Two years.

Mature plant: Height: 1.25 m. Width: 0.9 m.

Rootstock: 'Dr. Huey' in the USA. *Rosa Dumetorum* 'Laxa' for the observed plants in the U.K.

Foliage: Number of leaflets on normal mid-stem leaves: 5–7 (including terminal leaflet).

*Size.*—Medium. About 14.2 cm long×11.3 cm wide.

*Quantity.*—Normal. Average number leaves per flowering stem: 6–10, depending upon maturity of stem.

*Color.*—New foliage: Upper side: Greyed-Purple Group 187A. Lower side: Greyed-Purple Group 183C. Old foliage: Upper side: Yellow-Green Group 147A. Lower side: Green Group N138C.

Leaflets:

*Size.*—About 5.9 cm long×3.8 cm wide.

*Shape.*—Pointed oval.

*Base shape.*—Rounded.

*Apex shape.*—Acuminate.

*Texture.*—Smooth.

*Edge.*—Serrated.

*Serrations.*—Single, small.

*Petiole.*—Color: Yellow-Green Group 145A.

*Petiole rachis.*—Color: Yellow-Green Group 145B. Underside: Glandular.

*Stipules.*—Length: 2.5 cm, serrated.

*Auricle shape.*—Subulate.

*Disease resistance.*—Resistant to powdery and downy mildew, blackspot and rust in normal growing conditions.

*Pest resistance.*—Not tested.

*Vein color.*—Yellow-Green Group 145C.

*Venation pattern.*—Reticulate.

Wood:

*New wood.*—Color: Greyed-Purple Group 185A. Bark: Smooth.

*Old wood.*—Color: Yellow-Green Group 146A. Bark: Smooth.

Stems:

*Mature stem.*—Length: 30 cm. Diameter: 4–6 mm depending upon maturity of stem.

*Internode distance.*—4 cm.

Prickles:

*Quantity.*—On main canes from base: Ordinary, 4 per 5 cm stem length. On laterals from main canes: Ordinary, 6 per 5 cm per stem length.

*Form.*—Concave curved inward.

*Length.*—8 mm.

*Color when young.*—Orange-Red Group N34A.

*Color when mature.*—Orange-Red Group N34A.

Small prickles:

*Quantity.*—On main stalks: None. On laterals: None.

Winter hardiness: Not tested.

I claim:

1. A new and distinct variety of shrub rose plant substantially as herein shown and described, characterized particularly by its flowers in deep, rounded, many-petalled cups of deep pink color; having an Old Rose fragrance on a rounded shrub with arching stems, medium to tall in size; and its resistance to powdery and downy mildew.

* * * * *

UNITED STATES PATENT AND TRADEMARK OFFICE

CERTIFICATE OF CORRECTION

PATENT NO. : PP 17,685 P2
APPLICATION NO. : 11/263894
DATED : May 1, 2007
INVENTOR(S) : David C.H. Austin It is certified that error appears in the above-identified patent and that said Letters Patent is hereby corrected as shown below:

Title Page, item [57]

In the Abstract, first line, "as shown" should read -- as herein shown --, see specification filed on 10/31/05 at page 10, line 4.

In column 3, line 35, "90 100" should read -- 90-100 --.

Signed and Sealed this

Twenty-sixth Day of February, 2008

JON W. DUDAS
*Director of the United States Patent and Trademark Office*

UNITED STATES PATENT AND TRADEMARK OFFICE

CERTIFICATE OF CORRECTION

PATENT NO. : PP 17,685 P2
APPLICATION NO. : 11/263894
DATED : May 1, 2007
INVENTOR(S) : David C.H. Austin It is certified that error appears in the above-identified patent and that said Letters Patent is hereby corrected as shown below:

Title Page, item [57]

In the Abstract, first line, "as shown" should read -- as herein shown--.

In column 3, line 35, "90 100" should read -- 90-100 --.

This certificate supersedes the Certificate of Correction issued February 26, 2008.

Signed and Sealed this

Third Day of June, 2008

JON W. DUDAS
*Director of the United States Patent and Trademark Office*